United States Patent
Weiss

(10) Patent No.: US 6,402,734 B1
(45) Date of Patent: *Jun. 11, 2002

(54) APPARATUS AND METHOD FOR CANNULATING RETINAL BLOOD VESSELS

(76) Inventor: Jeffrey N. Weiss, Northwest Medical Plaza 5800 Colonial Dr., Suite 300, Margate, FL (US) 33063

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/109,454

(22) Filed: Jul. 2, 1998

(51) Int. Cl.[7] ............................................... A61M 31/00
(52) U.S. Cl. ...................... 604/521; 604/264; 604/272; 606/15; 606/4; 606/108
(58) Field of Search ............................ 606/108, 204.25, 606/44, 13, 15, 3, 5, 17, 166, 107, 4; 604/166, 500, 52

(56) References Cited

U.S. PATENT DOCUMENTS

| | | | | |
|---|---|---|---|---|
| 1,749,919 A | * | 3/1930 | Mierley | |
| 3,815,604 A | * | 6/1974 | O'Malley et al. | |
| 5,013,295 A | * | 5/1991 | Dubroff | 604/38 |
| 5,167,645 A | * | 12/1992 | Castillo | 604/272 |
| 5,345,937 A | * | 9/1994 | Middleman et al. | 128/657 |
| 5,628,734 A | * | 5/1997 | Hatfalvi | 604/272 |
| 5,632,740 A | * | 5/1997 | Koch et al. | 606/4 |
| 5,653,724 A | * | 8/1997 | Imonti | 606/169 |
| 5,716,363 A | * | 2/1998 | Josephberg | 606/107 |
| 5,741,226 A | * | 4/1998 | Strukel et al. | 604/35 |
| 5,785,645 A | * | 7/1998 | Scheller | 600/171 |
| 5,792,099 A | * | 8/1998 | DeCamp et al. | 604/51 |
| 5,817,075 A | * | 10/1998 | Giungo | 604/294 |
| 5,919,158 A | * | 7/1999 | Saperstein et al. | 604/49 |
| 5,941,877 A | * | 8/1999 | Steen et al. | 606/107 |
| 5,993,409 A | * | 11/1999 | Maaskamp | 604/22 |
| 6,039,715 A | * | 3/2000 | Mackool | 604/272 |

OTHER PUBLICATIONS

Curt A. Wiederhielm, et al., Pulsatile Pressures in the Microcirculation of Frog's Mesentery, Department of Physiology and Biophysics, University of Washington School of Medicine, Seattle, Washington.

(List continued on next page.)

Primary Examiner—Angela D. Sykes
Assistant Examiner—Cris Rodriguez
(74) Attorney, Agent, or Firm—Malin, Haley & DiMaggio, P.A.

(57) ABSTRACT

An apparatus and method for safely cannulating a retinal blood vessel is described. The apparatus consists of a micropipette, micromanipulator and positioner mounted to a base which is attached to a wrist rest commonly used in eye surgery. The micropipette is connected to tubing such that a medication may be injected through the micropipette into the blood vessel or conversely, a small quantity of material may be removed from a blood vessel. Alternatively, a catheter, wire or stent may be placed through the cannula to treat or diagnose an area remote from the insertion site. The ability to cannulate a retinal blood vessel should be efficacious in the treatment of vein and artery occlusion, ocular tumors and other retinal, vascular and optic nerve disorders that would benefit from diagnosis and/or treatment.

20 Claims, 3 Drawing Sheets

OTHER PUBLICATIONS

Norman Ashton, Injection of the Retinal Vascular System in the Enucleated Eye in Diabetic Retinopathy, Department of Pathology, Institute of Ophthalmology, London.

M. Peduzzi, et al., Abnormal Blood Rheology in Retinal Vein Occlusion, Department of Ophthalmology, University of Modena, Italy.

Murfa In, et al., Microperfusion Studies of The Retinal Vessels. Inhibition of Fluorescent Transport by Benemid, University of Illinois at Chicago Eye and Ear Infirmary, Chicago, Illinois, USA.

B. E. Alf and E. de Juan, Jr., In Vivo Cannulation of Retinal Vessels, Duke University Eye Center, Box 3802, and the Veterans Administration Medical Center, Durhm, North Carolina.

P. W. Johannsson, et al., Elecyronic Measurement of Red Cell Flow in Micropipettes, Division of Medical Biophysics, Faculty of Medicine, The University of Calgary, Calgary, Alta., Canada.

* cited by examiner

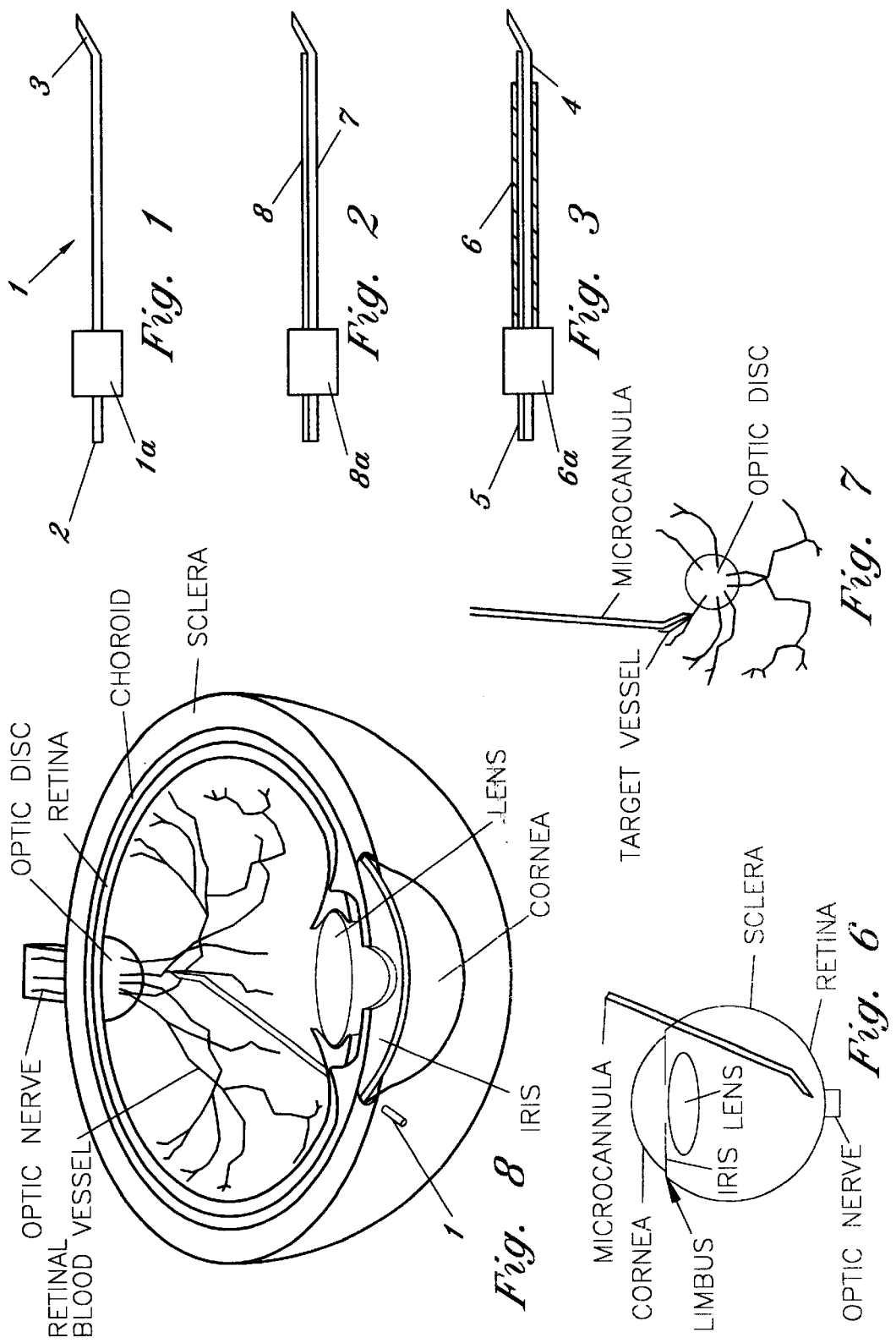

APPARATUS AND METHOD FOR CANNULATING RETINAL BLOOD VESSELS

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

This invention was disclosed in the Disclosure Documents Program of the U.S. Patent and Trademark Office on May 4, 1998, Disclosure Document No. 435938.

1. Field of the Invention

This invention relates to medical diagnostic and therapeutic methods and, in particular, to a method for cannulating a retinal blood vessel such that a medication may be injected or a quantity of fluid removed from the blood vessel. Alternatively, a catheter, wire or stent may be placed through the cannula to treat or diagnose an area remote from the insertion site.

2. Description of Related Art

The cannulation of a retinal blood vessel is difficult as the lumen of the blood vessels are less than 200 microns in size. The present day ocular instruments are too large to cannulate the vessel and the dexterity required to maintain the cannula within the blood vessel for several minutes is not commonly available. The piercing of a blood vessel elsewhere in the body to inject medications, perform surgical procedures or remove blood for analysis and treatment is commonly performed. It is therefore, to the effective resolution of the aforementioned problems and shortcomings that the present invention is directed.

Accordingly, it is an object of this invention to provide a microcannula or micropipette whose lumen is small enough to be safely placed within the lumen of a retinal blood vessel and by its configuration is parallel to the lumen when placed through a standard sclerotomy site, as commonly used in vitreoretinal surgery. The terms microcannula and micropipette are used interchangeably throughout the application. To the extent that such terms differ in any way in meaning, if any, then the broadest definition of the two terms is considered to be the definition for both terms for purposes of the instant invention disclosure.

It is another object of this invention to provide, by its configuration and method of attachment, a stable support such that the micropipette may be securely held within the blood vessel so that subsequent maneuvers may be safely accomplished.

It is still another object of this invention to provide a micromanipulator such that the micropipette may be remotely advanced to perforate the retinal blood vessel.

It is yet another object of this invention to provide a portable device that may be easily attached to a standard operating surgical wrist rest and is stable in its "X", "Y" and "Z" planes.

It is a further object of this invention to provide a device that, by its configuration and method of attachment, does not inhibit the surgeon's view when using an operating microscope or otherwise interfere with the use of the operating microscope.

It is yet another object of this invention to provide a safe method such that the surgical procedure may be performed.

BRIEF SUMMARY OF THE INVENTION

The foregoing objects are achieved and the foregoing problems are solved in one illustrative embodiment of the invention in which a retinal blood vessel is cannulated using a micropipette (microcannula) attached to a micromanipulator which is connected to a positioner attached to a standard surgical wrist rest.

More particularly, a sclerotomy is made at the standard distance from the limbus and an illuminated infusion cannula is placed through the sclera at this point. A pars plana vitrectomy may or may not be necessary with further experience. Another sclerotomy is made at the standard distance from the limbus such that the micropipette/microcannula is parallel to the retinal blood vessel chosen to be cannulated. The micropipette is then placed through the sclerotomy overlying the selected retinal blood vessel. The intraocular pressure is lowered to approximately 5 mm of Mercury to allow dilation of the vessel. Once the blood vessel is perforated, it may be advantageous to raise the intraocular pressure to minimize bleeding. The retinal blood vessel may be cannulated manually or the micromanipulator used to advance the micropipette into the retinal blood vessel.

The micropipette tip is preferably at a 135 degree angle to the shaft such that it is parallel to the lumen of the blood vessel when placed through a standard sclerotomy site. The tip of the micropipette is preferably 100 microns in diameter or smaller so it may safely enter the lumen of the retinal blood vessel. The opposite end of the micropipette can be connected to and in fluid communication with a standard surgical tubing and syringe such that fluid may be withdrawn or injected into the retinal vessel. Alternatively, a catheter or wire may be advanced through the microcannula for diagnosing, testing or treatment of an area located at a distance from the insertion site.

In certain situations medication such as Tissue Plasminogen Activator ("TPA") made by Genetech, Inc. and sold under the trademark ACTIVASE can be injected into the retinal vessel. Alternatively, a dye can be injected into the retinal vessel for diagnosing purposes.

The micromanipulator is preferably attached to a positioner that is freely mobile and stable in the "X", "Y" and "Z" directions. In the preferred embodiment, the positioner is securely attached to a standard ophthalmic surgery wrist rest by conventional means. The positioner is easy to attach to the wrist rest and may be removed when the device is not needed. At the conclusion of the maneuver, the intraocular pressure is raised In order to minimize retinal hemorrhaging and the micropipette removed from the blood vessel. The operation is then concluded in standard fashion.

In accordance with these and other objects which will become apparent hereinafter, the instant invention will now be described with particular reference to the accompanying drawings.

BRIEF DESCRIPTION OF THE SEVERAL VIEWS OF THE DRAWINGS

The invention may be better understood by reference to the drawings in which:

FIG. 1 is a front view of a first embodiment for the micropipette (microcannula) of the present invention;

FIG. 2 is a front view of a second embodiment of the micropipette in which an illumination member such as a fiberoptic light source is attached to the side of the micropipette to provide illumination during the operation;

FIG. 3 is a front view of a third embodiment of the micropipette wherein the micropipette and fiberoptic are enclosed within a protective sheath or tube to minimize breakage when placed into the eye;

FIG. 6 illustrates a view of the micropipette when placed through the sclerotomy site into the eye;

FIG. 7 illustrates the tip of the micropipette overlying and parallel to the retinal blood vessel to be cannulated; and FIG. 8 is a perspective view of the micropipette when placed through the sclerotomy site into the eye.

DETAILED DESCRIPTION OF THE INVENTION

Figure 4:
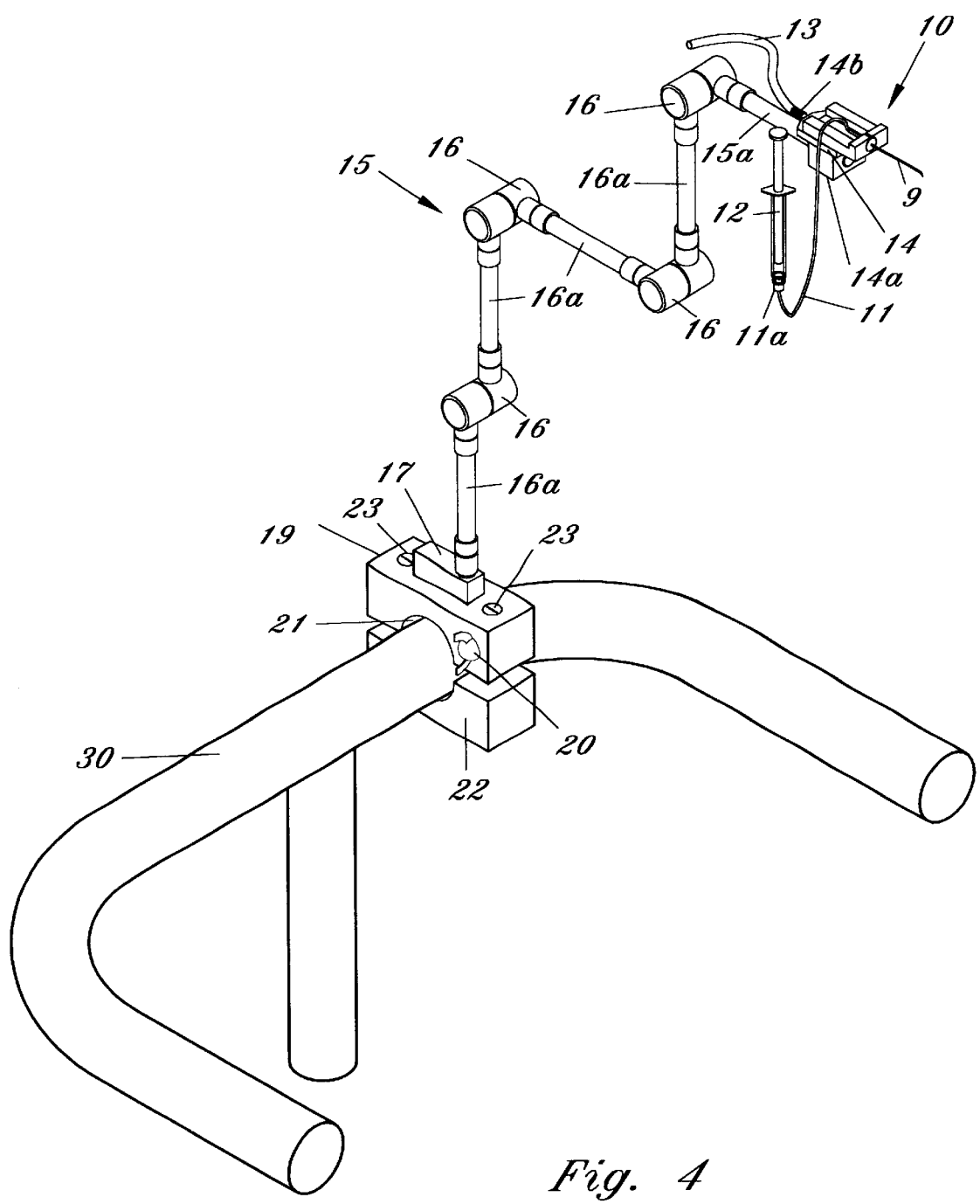
FIG. 4 is a perspective view of the preferred embodiment for the micropipette, micromanipulator, positioner and base of the present invention attached to a conventional wrist rest.

FIG. 1 illustrates a first embodiment for the micropipette/microcannula (1) showing the opening (2) that is preferably connected to a surgical tubing and the tip (3) of the micropipette oriented at an approximately 135 degree angle, although other ranges are possible. Tip (3) is angled so that it may safely cannulate the retinal vessel when micropipette (1) is placed through a standard retinal surgical sclerotomy site. While glass is suggested for the material because of its ease of fashioning, strength, transparency, etc., other materials may be used. It is essential, however, that the material maintain substantial strength when fashioned to perform retinal vessel cannulation. A handle (1a) is shown attached to the body member of micropipette (1). Handle (1a) fits securely within a micropipette holder (10) by inserting the end of micropipette (1) associated with handle (1a) and handle (1a) into the front opening of holder (10). Once inserted micropipette (1) is held in place by a set screw associated with the holder (10).

As seen in FIG. 2, an alternative embodiment of the micropipette/microcannula is illustrated. In this embodiment, a fiberoptic (8) is attached to the micropipette body (7) to provide illumination such that an illuminated infusion cannula is not required. If a vitrectomy is not performed then one sclerotomy for the micropipette and fiberoptic is all that is necessary. A handle (8a) is provided and fits securely within the holder (10) and is held in place by a set screw within the holder (10), similar to as described for micropipette (1).

FIG. 3 illustrates a further alternative embodiment for the micropipette (4) where a fiberoptic for illumination is included (5) and both items are placed within a tube or needle (6). The purpose of the tube or needle is to protect the enclosed instruments such that they may be safely inserted through the sclerotomy site without breakage. Both the fiberoptic and the micropipette ends are at the end or protrude from the end of the tube or needle. The micropipette and fiberoptic may be advanced through the end of the tube or needle once it has been placed within the eye. A handle (6a) is illustrated that fits securely within the holder (10) and may be firmly held in place by a set screw or locking mechanism within the holder (10), as previously described above. If a vitrectomy is not performed then one sclerotomy for this device is all that is necessary.

FIG. 4 illustrates the micropipette (9) attached to the holder (10). A screw handle (14b) which controls the position of the holder (10) is attached to a flexible tube (13) so the micromanipulator may remotely advance the micropipette. Screw handle (14b) is associated with a micromanipulator (14). Preferably, screw handle (14b) is connected to micromanipulator (14). Holder (10) is attached to the micromanipulator. In one embodiment, the micromanipulator is a miniature translation stage, using dual dowel pin bearings. One such micromanipulator is made by the Newport Corporation located in Irvine, Calif. The Newport micromanipulator has a stage which has a range of travel of approximately four (4 mm) millimeters.

Figure 5:
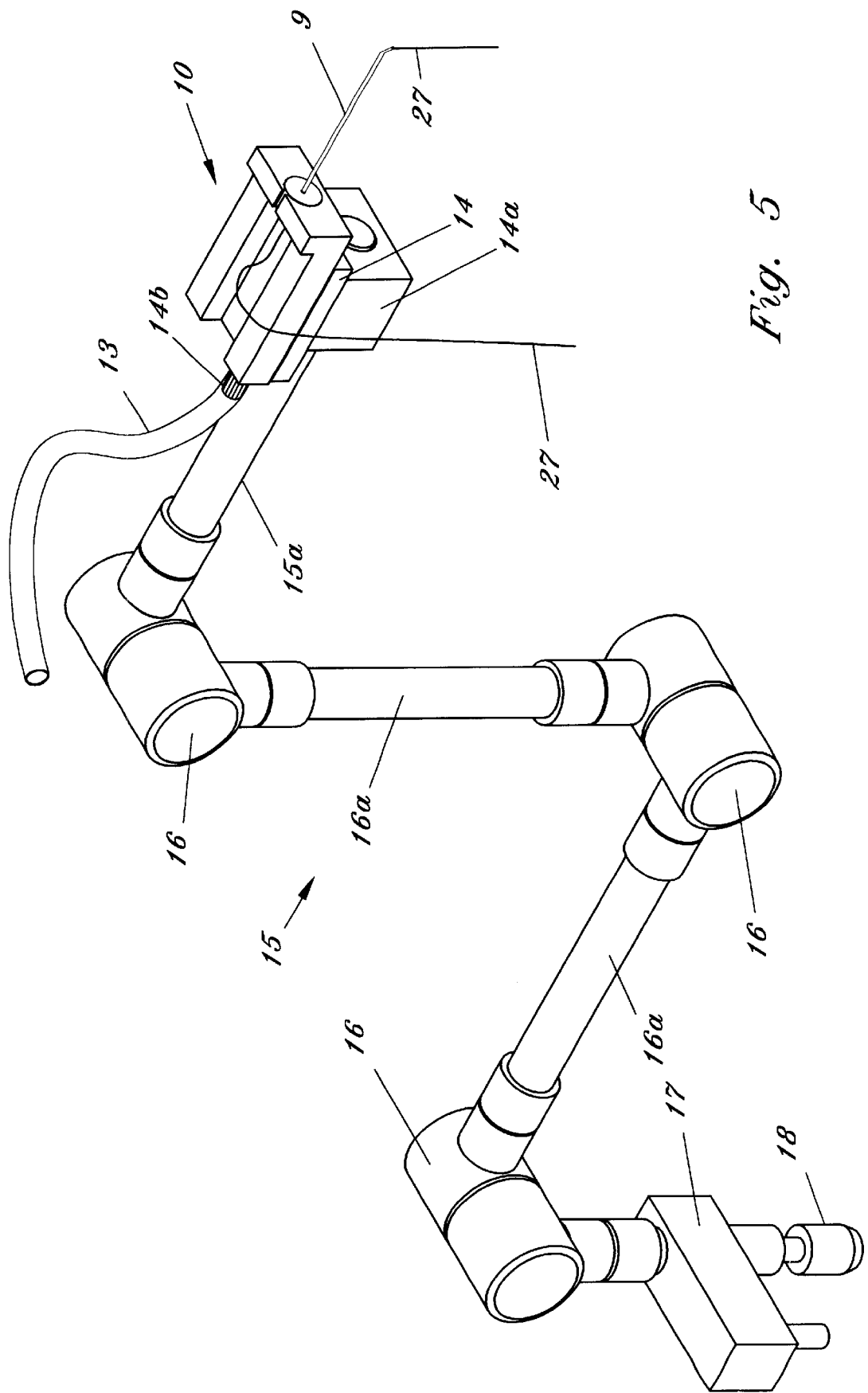
FIG. 5 is another perspective view of the preferred embodiment for the micropipette, micromanipulator, positioner and base of the present invention.

In one embodiment (FIG. 4), the non-tip end of the micropipette is preferably attached to standard surgical tubing (11). The tubing (11) is attached to a connector (11a) which is connected to a syringe (12) that is used to inject medication or withdraw fluid from the retinal blood vessel. In certain situations medication such as TPA can be injected into the retinal vessel. Alternatively, a dye can be injected into the retinal vessel for diagnosing purposes. Alternatively, a catheter, wire or stent (27) may be advanced through the microcannula for diagnosing, testing or treatment of an area located at a distance from the insertion site (FIG. 5).

It should also be apparent to those skilled in the art that the micromanipulator and injector or withdrawing device may be electrically controlled by a foot pedal or other switch so it maybe activated by the surgeon. These alternative embodiments are considered within the scope of the invention.

The micromanipulator (14) is attached to a base (14a) which is attached to a positioner (15) that is freely mobile in the "X", "Y" and "Z" planes due to the multiplicity of joints (16), connected by elongated members (15a and 16a). It would be apparent to those skilled in the art that the positioner may also be electrically controlled by servo-motors and activated by the surgeon with a foot pedal or other switch. Such alternatives are also considered within the scope of the invention. Positioner 15 is not limited to any specific amount of elongated members.

The positioner can be attached to a base (17). In one embodiment, an attachment post (18) fits into a hole within another base (19). Preferably, set screws or wing nuts (20), are provided, on either side of the base which is used to secure the post to the base. In order to make the base secure base (19) attaches to another base (22) by two screws (23). Base (19) fits above the standard ophthalmic surgical wrist rest (30) which is oriented perpendicular to bases (19) and (22). The wrist rest fits within the hole (21) that exists between bases (19) and (22). Base portion (22) completes the base and is located underneath the wrist rest. Alternatively, the positioner may be attached directly to the wrist rest or connected to the operating microscope or operating table. Additionally, the bases can be sized to fit other objects in the operating room. Changes in modifications within the spirit and scope of the invention will be apparent to those skilled in the art. Such modifications and changes are intended to be covered by the claims herein.

Thus, the present invention provides a device that may safely advance the micropipette into the retinal blood vessel while securely holding it in a stable fashion and allowing rotation in the "X", "Y" and "Z" planes for ease of maneuverability. The apparatus can be easily attached and removed from the operating field, and, thus, portable. The apparatus can be attached by conventional means to the a wrist rest, the operating table, the operating microscope or any other convenient and stable location in the operating room. Additionally, the apparatus is constructed so not to encumber the surgeon's view through the operating microscope, or otherwise interfere with the use of the operating microscope.

In all embodiments, the micropipette/microcannula is preferably designed to fit a standard twenty (20) gauge sclerotomy site. However, such is not limiting and other gauge sclerotomy sites can be chosen, and the micropipette designed accordingly, and are considered within the scope of the invention.

Though not to be considered limiting, the dimensions for the micropipette/microcannula for all embodiments, can preferably consist of the following:

(a) first body portion associated with beveled tip end—length approximately 750 microns;

(b) tip end beveled at approximately twenty (20°) degrees;

(c) second body portion associated with handle—length approximately 62–70 millimeters;

(d) beveled tip end—outer diameter approximately 100 microns—inner diameter approximately 72 microns;

(e) opposite end—outer diameter approximately 1 millimeter—inner diameter 0.69 millimeter; and (f) angle between first body portion and second body portion approximately 130°–140°.

As seen in FIGS. 6–8, a sclerotomy is made at the standard distance from the limbus and an illuminated infusion cannula is placed through the sclera at this point. A pars plana vitrectomy may or may not be necessary with further experience. Another or second sclerotomy is made at the standard distance from the limbus such that the micropipette/microcannula is parallel to the retinal blood vessel chosen to be cannulated. The micropipette is then placed through the sclerotomy overlying the selected retinal blood vessel. The intraocular pressure may be lowered to approximately 5 mm of Mercury to possibly allow dilation of the vessel. Once the blood vessel is perforated, it may be advantageous to raise the intraocular pressure to minimize bleeding. The retinal blood vessel may be cannulated manually or the micromanipulator used to advance the micropipette into the retinal blood vessel.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A method for cannulating a retinal blood vessel, said method comprising the steps of:

(a) providing a sclerotomy site at a distance from a limbus of an eye associated with the retinal blood vessel to be cannulated;

(b) inserting a small cannula within the eye such that the cannula is overlying the retinal blood vessel;

(c) inserting the cannula within the lumen of the retinal blood vessel; and (d) introducing medication through the cannula, removing material from the blood vessel through the cannula or inserting a catheter, wire or stent through the cannula.

2. The method for cannulating a retinal blood vessel of claim 1 further including the steps of inserting an illuminated infusion cannula through the sclerotomy site and providing a second sclerotomy site for inserting the small cannula within the eye.

3. The method for cannulating a retinal blood vessel of claim 1 further including the step of lowering intraocular pressure to cause dilation of the retinal blood vessel prior to inserting the micropipette within the lumen of the blood vessel.

4. The method for cannulating a retinal blood vessel of claim 3, further comprising the step of raising the intraocular pressure when the cannula is removed from the blood vessel to minimize hemorrhaging.

5. A microcannula for use in cannulating retinal blood vessels and retinal surgery, said microcannula comprising:

an elongated non-bendable, relatively rigid hollow body member having a single angled first end to define a relatively sharp beveled tip and a second end, said second end attached to a flexible tubing member, said body member having a first body portion associated with said beveled tip and a second body portion associated with said second end, said first body portion monolithically formed with said second body portion;

wherein said first body portion having a first length and said second body portion having a second length; wherein the first length is substantially smaller in size than the second length;

wherein the first end of said body member is insertable through a retinal surgical sclerotomy site without being attached to the sclerotomy site, said beveled tip perforating a targeted retinal structure, wherein said first body portion is permanently disposed at an angular relationship with said second body portion such that the beveled tip is positioned substantially parallel to the targeted retinal structure to be perforated when the body member is inserted through a sclerotomy site;

wherein said angular relationship is chosen based on a specific area of a person's retina targeted for surgery;

wherein said body member being sized such that the beveled tip can safely enter into the retinal structure;

wherein the length of said first body portion and said beveled tip causing a shelved incision in the targeted retinal structure which is self sealing upon removal of said first body portion and said beveled tip from a perforation site.

6. The microcannula of claim 5 further including a means for attaching said body member to a stabilization system; wherein said means for attaching is a fixed handle attached to said body member at a point along said second portion near said second end.

7. The microcannula of claim 5 further including an illumination member attached to said body member.

8. The microcannula of claim 7 wherein said illumination member is a fiberoptic.

9. The microcannula of claim 5 wherein said body member is adapted for fluid communication with a tube and syringe associated with the tube.

10. The microcannula of claim 5 wherein said angular relationship is approximately 135 degrees.

11. The microcannula of claim 5 wherein said body member is constructed from glass.

12. The microcannula of claim 5 wherein said body member having an outer diameter of approximately 100 microns at its beveled end.

13. The microcannula of claim 5 wherein said elongated hollow body member having a diameter of approximately 100 microns at its beveled end.

14. The microcannula of claim 5 wherein said tip is beveled at an angle of approximately 20 degrees.

15. The microcannula of claim 5 wherein an outer diameter of a first end of said body member is smaller than an outer diameter of a second end of said body member.

16. The microcannula of claim 5 further including a protective outer tube, at least a portion of said body member disposed within said protective outer tube.

17. The microcannula of claim 5 wherein said body member having an outer diameter of no greater than approximately 100 microns at its first beveled end and an outer diameter of approximately 1 millimeter at its second end.

18. A microcannula for use in cannulating retinal blood vessels and retinal surgery, said microcannula comprising:

a relatively rigid elongated hollow body member having a single angled first end to define a relatively sharp beveled tip and a second end, said second end attached to a flexible tubing member, said body member having a first body portion associated with said beveled tip and a second body portion associated with said second end, said first body portion monolithically formed with said second body portion, said tip beveled at an angle of approximately 20 degrees, said body member having an outer diameter of no greater than approximately 100 microns at its first beveled end and an outer diameter of approximately 1 millimeter at its second end;

wherein the first end of said body member insertable through a retinal surgical sclerotomy site without being attached to the sclerotomy site, wherein said first body portion is disposed at a permanent angular relationship with said second body portion such that the beveled tip is positioned substantially parallel to a targeted retinal structure when the body member is inserted through a sclerotomy site; wherein said angular relationship is chosen based on a specific area of a person's retina targeted; wherein an outer diameter at said first end of said body member is smaller than an outer diameter at said second end of said body member;

wherein said first body portion having a first length and said second body portion having a second length; wherein the first length is smaller in size than the second length;

wherein said body member being sized such that the beveled tip and first portion of said body member can safely enter into the retinal structure;

wherein the length of said first body portion and the angle of said beveled tip causing a shelved incision in the targeted retinal structure which is self sealing upon removal of said first body portion and said beveled tip from the perforation site.

19. A microcannula for use in cannulating retinal blood vessels and retinal surgery, said microcannula comprising:

an elongated non-bendable, relatively rigid hollow body member having a single angled first end to define a relatively sharp beveled tip and a second end, said second end is associated with a tubing member, said body member having a first body portion associated with said beveled tip and a second body portion associated with said second end;

wherein said first body portion having a first length and said second body portion having a second length; wherein the first length is substantially smaller in size than the second length;

wherein the first end of said body member is adapted for insertion through a retinal surgical sclerotomy site without being attached to the sclerotomy site, said beveled tip adapted for perforation of a targeted retinal structure, wherein said first body portion is permanently disposed at an angular relationship with said second body portion such that the beveled tip is adapted for substantially parallel positioning to the targeted retinal structure to be perforated when the body member is inserted through a sclerotomy site;

wherein said angular relationship is chosen based on a specific area of a person's retina targeted for surgery;

wherein said body member being sized such that the beveled tip can safely enter into the retinal structure;

wherein the length of said first body portion and said beveled tip allow for a shelved incision which is self sealing upon removal of said first body portion and said beveled tip from a perforation site; and a protective outer tube, at least a portion of said body member disposed within said protective outer tube;

wherein said body member movably disposed within said protective outer tube to allow said tip to be moved between extended to retracted positions with respect to said protective outer tube.

20. A microcannula for use in cannulating retinal blood vessels and retinal surgery, said microcannula comprising:

a substantially rigid hollow body member having a substantially sharp beveled tip first end and a second end, said body member having a first body portion associated with said beveled tip and a second body portion associated with said second end, said first body portion having a first length and said second body portion having a second length;

wherein the first length is substantially smaller in size than the second length; wherein said first body portion is permanently disposed at an angular relationship with said second body portion; and a protective outer tube, at least a portion of said body member disposed within said protective outer tube;

wherein said body member movably disposed within said protective outer tube to allow said tip to be moved between extended to retracted positions with respect to said protective outer tube.

* * * * *